United States Patent [19]

Clark, Jr.

[11] 4,040,908

[45] Aug. 9, 1977

[54] POLAROGRAPHIC ANALYSIS OF CHOLESTEROL AND OTHER MACROMOLECULAR SUBSTANCES

[75] Inventor: Leland C. Clark, Jr., Cincinnati, Ohio

[73] Assignee: Children's Hospital Medical Center, Cincinnati, Ohio

[21] Appl. No.: 666,252

[22] Filed: Mar. 12, 1976

[51] Int. Cl.$^2$ ............................................. G01N 31/14
[52] U.S. Cl. .............................. 195/103.5 R; 195/63; 195/103.5 C; 204/1 E; 204/195 P
[58] Field of Search ................ 195/103.5 R, 103.5 C; 204/1 E, 195 P, 195 B

[56] References Cited

U.S. PATENT DOCUMENTS

| 3,539,455 | 11/1970 | Clark | 204/195 P |
|---|---|---|---|
| 3,542,662 | 11/1970 | Hicks et al. | 195/103.5 R |
| 3,607,093 | 9/1971 | Stone | 195/103.5 R |
| 3,857,771 | 12/1974 | Sternberg | 195/103.5 R |
| 3,907,645 | 9/1975 | Richmond | 195/103.5 R |

Primary Examiner—Alvin E. Tanenholtz
Assistant Examiner—C. A. Fan

Attorney, Agent, or Firm—Wood, Herron & Evans

[57] ABSTRACT

A micro-method for measurement of sterols such as cholesterol, and other macromolecular substances, is disclosed utilizing enzymes for the conversion of such substances to produce ultimately hydrogen peroxide and measurement of the generated hydrogen peroxide with a membrane covered polarographic anode. The polarographic anode is set at a voltage so as to produce current proportional to hydrogen peroxide concentration. According to the method of this invention, the macromolecular substance under analysis enters into an enzymatic reaction in a sample chamber on the side of the membrane opposite the anode and the membrane is impermeable to such substances, but senses hydrogen peroxide. The method is adapted to measure free and total blood cholesterol in a precise, rapid, sensitive and specific manner. Other substances of a macromolecular or conventional membrane impermeable nature such as high molecular weight starches or proteins, which undergo enzymatic reaction to produce ultimately hydrogen peroxide, may be analyzed by employing this polarographic technique.

23 Claims, 4 Drawing Figures

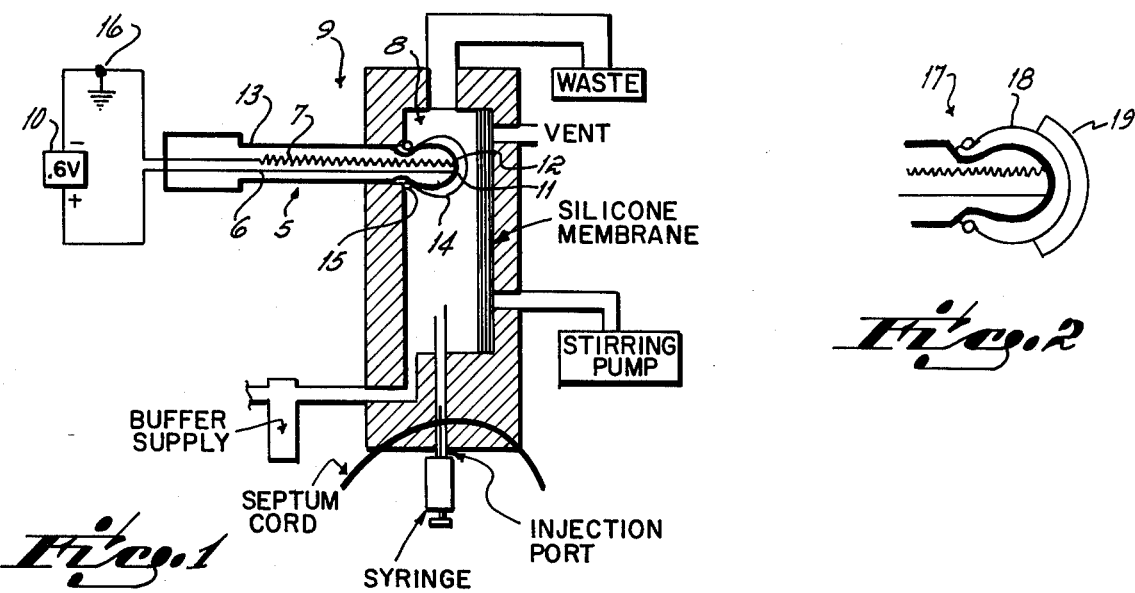
FIG. 1
FIG. 2
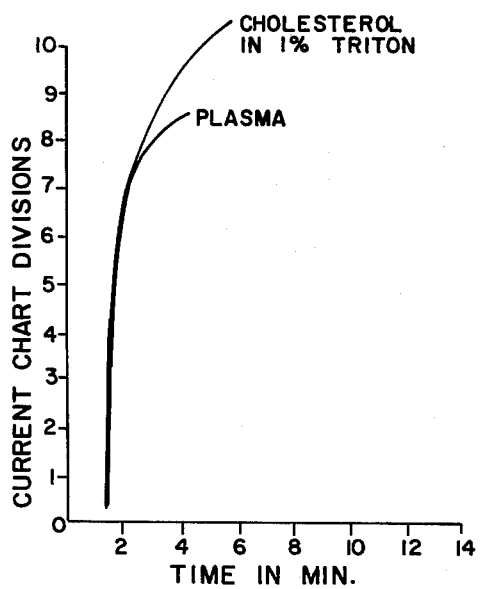
FIG. 3
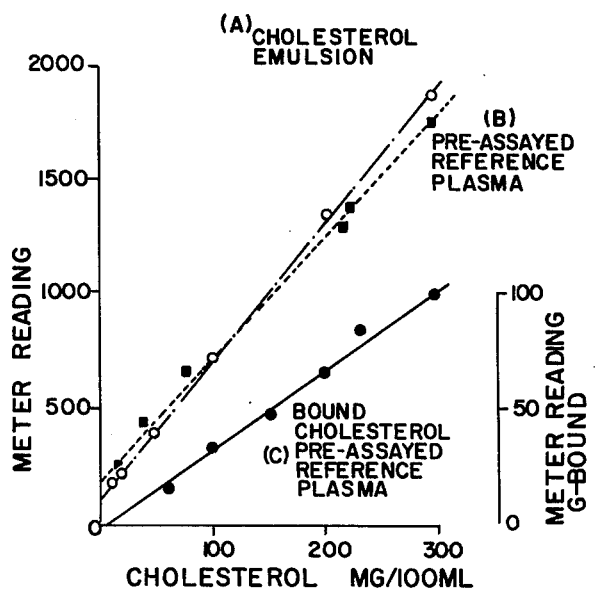
FIG. 4

POLAROGRAPHIC ANALYSIS OF CHOLESTEROL AND OTHER MACROMOLECULAR SUBSTANCES

BACKGROUND OF THE INVENTION

Considerable effort has heretofore been devoted to analytical techniques for biomedical and industrial applications. Analytical techniques are of crucial importance in these areas of application, including clinical diagnosis. For example, over the past two decades, the relationship between cholesterol, triglyceride, and atherosclerosis has been established and clarified. Initial ascertainment of an elevation of cholesterol or triglyceride leads to more detailed evaluation of lipid and lipoprotein classes useful in diagnosis and treatment. Screening procedures for quantitation of plasma cholesterol are highly important as a primary approach to an amelioration of atherosclerosis. Because of the close association of cholesterol and atherosclerosis, multiple approaches for measurement of plasma cholesterol have been examined. Currently, colorimetric methods involving isopropanol extraction and saponification are being widely used and have been automated to allow reasonable precision and accuracy at a rate of 30 samples per hour. The colorimetric methodology is expensive, relatively non-specific, subject to interference from even slight changes in humidity and bilirubin levels, and requires the use of highly corrosive agents such as concentrated sulfuric acid, acetic anhydride and acetic acid. Colorimetric methods also require at least 5-10 cc blood sampling with requisite venipuncture.

Recently two major approaches to improve methodology for cholesterol quantitation have been made utilizing gas-liquid chromatography (GLC) and enzymatic measurement. The GLC techniques are highly specific for cholesterol, and are precise, accurate, and very sensitive. No preparatory organic solvent extraction is required, but saponification is a necessary step. The GLC methods are also true micro-methods requiring as little as 10-50 microliters of plasma, well within the range of capillary sampling. The GLC methodologies still require relatively expensive machinery which may be automated, and expert technical supervision to maintain precision.

The enzymatic methods, heretofore used, have combined two enzymes, cholesterol oxidase (CO) and cholesterol ester hydrolase (CE), with colorimetric techniques. These colorimetric methods rely on enzymatic conversion of cholesterol or its esters to cholestenone and hydrogen peroxide, and then on the reaction of the peroxide with various compounds to produce measurable chromogens or fluorogens.

About 15 years ago, enzyme-coupled electrodes were reported for the polarographic analysis of substances. For example, in my U.S. Pat. No. 3,539,455 a membrane polarographic electrode system and method was described for the rapid and accurate quantitative analysis of substances which theretofore posed difficulties in analyzing directly by polarographic methods. According to the description in my mentioned patent, small molecular substances, such as glucose were measured with a membrane polarographic electrode system. By use of cellulose or another membrane which is permeable to small molecules, such as glucose, but is impermeable to proteins, the membrane keeps glucose oxidase enzyme on the side of the membrane with the anode for reaction with glucose. Therefore, for example, if a sample of blood were placed on the membrane side opposite the electrode, with an aqueous solution of the enzyme and oxygen on the electrode side of the membrane, the low molecular weight materials, such as glucose, pass from the blood samples through the membrane for enzymatic reaction adjacent the electrode. After a certain period of time a steady state is reached when the hydrogen peroxide concentration is directly proportional to the glucose concentration and the cell produces a current flow as a function of the amount of hydrogen peroxide being formed which serves as an indication of the amount of glucose present. As disclosed in my article entitled "Electrode Systems for Continuous Monitoring in Cardiovascular Surgery", N.Y. Academy of Sciences, Vol. 102, pp. 29-45 (1962), the Clark oxygen electrode can be arranged so that it is sensitive to glucose by virtue of the fact that oxygen is consumed by enzymatic reaction in proportion to glucose content. In such arrangement, the inner membrane is impermeable to glucose and the reaction is monitored by drop in oxygen. However, my previous membrane polarographic techniques for measurement of by-product $H_2O_2$ were limited to the detection of small molecules which were capable of permeating the membrane for enzymatic reaction with an enzyme being contained on the electrode side of the membrane.

SUMMARY OF THE INVENTION

This invention is predicted in part upon the discovery that a membrane polarographic anode even though having a membrane impermeable to macromolecules, such as cholesterol, may be used to obtain precise, accurate, sensitive and specific measurements of such macromolecules. Particularly, it has been found that when such macromolecules are converted by at least one enzyme to produce ultimately hydrogen peroxide in a sample chamber on the side of the membrane opposite the electrode, at least a portion of the hydrogen peroxide will diffuse into the membrane into contact with the electrode and the current flowing across the cell can be determined as a measure of the rate of formation of the hydrogen peroxide and as an indication of the amount of macromolecules present in the material under analysis.

Therefore, this invention provides a technique for quantitatively analyzing macromolecules not heretofore felt possible to quantitate by membrane polarographic technique. No membranes are known which have the desired permeability by macromolecules to thereby permit use of previous membrane polarographic techniques. However, it has been discovered that a reaction between an enzyme and a macromolecule, though impassable by a polarographic membrane, can occur either within the membrane or in such intimate proximity thereto such that the rate of formation of $H_2O_2$ can be measured by a polarographic anode as an accurate indication of the amount of the macromolecule present. Such a result has not been heretofore predicted or appreciated in membrane polarographic technique.

A number of advantages are provided by this invention. In the case of cholesterol, as developed above, the measuring method in wide use today is an automated colorimetric method, and it is expensive to perform, subject to interference from a number of common substances, and requires the use of highly corrosive reagents. It also requires blood samples of at least 5-10 cc and the drawing of such samples is fairly expensive and painful. In contrast, the method according to this invention uses simple and inexpensive equipment, allows precise, accurate, sensitive and specific measurement of cholesterol in 10-50 microliters or less of plasma without the need for saponification, corrosive reagent, or considerable technial expertise. Accordingly, the benefits of this invention particularly are uniquely obtained with respect to the determination of cholesterol, both total and free cholesterol, in plasma with considerable ease and advantage. Because the desirable electrode response depends upon measurement of the rate of the reaction and not upon complete stoichiometric conversion of the cholesterol ester to cholesterol and cholesterol to peroxide, most determinations can be made in less than four minutes. Thus, macromolecules heretofore undetected by precise and rapid means may be quantitated by my method.

Other macromolecules may be analyzed according to the principles of this invention. For example, macromolecules of starch can be broken down by amylase, and certain other hydrolytic enzymes, whereupon the smaller by-products such as glucose or galactose can be acted upon by glucose oxidase which, in turn, provides hydrogen peroxide for detection on the opposite side of the membrane as an indication of the amount of starch present. Thus, the invention provides a method for quantitative polarographic determination of such macromolecules which are convertible by at least one enzyme to produce ultimately hydrogen peroxide. Among the class of such substances are sterols, including cholesterol, beta sitosterol, campesterol and stigmasterol; other macrmolecules such as polysaccharides including starches; proteins, polypeptides and other polymeric materials. In the case of the enzyme cholesterol oxidase, it is specific for sterols having a Δ4 or Δ5 double bond and 3-betahydroxy group on the A ring. The enzymatic method is therefore quite specific for blood cholesterol since it is the predominant 3-betahydroxy sterol in human blood. However, other enzyme-macromolecular reactions may be employed for quantitative determinations with my method.

Accordingly, in one of its broader aspects, this invention is directed to a method for quantitative polarographic (voltammetric) determination of a substance which is convertible by at least one enzyme to produce ultimately hydrogen peroxide. A polarographic cell is provided including at least one electrode sensitive to hydrogen peroxide and an electrolyte. The sensing electrode is positioned behind a membrane which is both permeable to hydrogen peroxide and impermeable to the substance being measured. At least one enzyme is contained in the cell on the sample chamber side of the membrane opposite the electrode for enzymatic reaction with the substance under analysis to produce ultimately hydrogen peroxide. A potential is established across the cell such that current is produced which is proportional to the amount of the hydrogen peroxide produced. Into such a membrane polarographic cell, a quantity of material containing a substance to be measured is added for enzymatic reaction on the side of the membrane opposite the electrode and to effect diffusion of at least a portion of the hydrogen peroxide into the membrane and into contact with the electrode. Then, the current flowing across the cell is determined as a function of the amount of hydrogen peroxide formed and as an indication of the amount of the substance in the material. The current flowing is a measure of the rate of formation of the hydrogen peroxide by enzymatic reaction with the substance being analyzed.

In a preferred form for quantitative polarographic determination of cholesterol, the method depends upon the consecutive or simultaneous reaction of cholesterol oxidase (CO) and cholesterol esterase (CE) with cholesterol and its esters to produce cholestenone and hydrogen peroxide, which is then detected by a hydrogen peroxide sensing polarographic platinum anode. When it is desired to measure first one substance, such as free cholesterol, the enzyme cholesterol oxidase may be used first then, a second substance, such as cholesterol ester, may be determined using cholesterol esterase to convert esters to free cholesterol. Alternatively, both enzymes can be used in concert so that all reactions are proceeding at the same time; for example, esterase and oxidase added simultaneously provide an electrode response equivalent to that obtained with temporally separate exposure to the enzymes.

The method is especially useful for measuring cholesterol in serum with the advantages obtained as described above. Also, in another method form, whole blood samples may be analyzed. For example, where enzyme is added to the sample chamber solution containing whole blood samples, the blood's high catalase activity tends to destroy the hydrogen peroxide as rapidly as it is formed by the oxidase. It has been found, however, that the catalase activity of slightly hemolyzed plasma can be overcome by the use of an agent such as sodium azide. For example, in slightly hemolyzed blood having about 20-200 mg% hemoglobin, azide or similar agent can be added to inhibit catalase activity. It has also been discovered that the azide inhibits the spontaneous decomposition of hydrogen peroxide and by virtue of its bacteriocidal properties, it also preserves buffer which is added to control pH. Therefore, this invention provides a method which makes possible new rapid means for measuring cholesterol in plasma and slightly hemolyzed plasma.

In another of its embodiments, whole blood samples may be analyzed using a new electrode structure and method in the determination of macromolecules by the membrane polarographic technique. As developed above, the enzyme-directed reaction in the determination of cholesterol takes place "outside" the polarographic membrane, i.e., on the side opposite the electrode, and the enzyme is also contained on that side. Therefore, the enzymes may be added to the cell solution on the membrane side opposite the electrode. Where the enzymes are not immobilized, they must be thrown away after each measurement, substantially increasing the cost of each analysis. Accordingly, in another preferred embodiment, it has been found that the enzymes can be immobilized by binding one or more of them either to the outer surface of the electrode membrane or in the sample chamber. In this form, with immobilized enzymes, the electrodes can be reused and this makes possible the use of even more costly, higher purity enzymes which also improve the speed and sensitivity of the electrode. Furthermore, the immobilization itself helps to stabilize labile enzymes so that they can provide more reproducible results and fewer controls need to be run. The membrane immobilized enzymes have also been found to permit analysis of whole blood samples directly.

The invention will be further understood and its advantages appreciated with reference to the following detailed description and drawings in which:

FIG. 1 is a diagrammatic illustration of a polarographic instrument and other means employed in the methods of this invention showing the overall arrangement of the electrical circuit, polarographic cell and sample chamber with sample chamber illustrated in partial cross-section.

FIG. 2 is an optional form of the type of the electrode probe shown in FIG. 1 and diagrammatically illustrating enzyme immobilization.

FIG. 3 is a polarographic curve showing a plot of the current versus the time for a plasma and artificial plasma sample.

FIG. 4 is a plot of the current versus cholesterol concentration of preassayed reference samples for both the electrode probe structure of FIG. 1 and the bound enzyme structure of FIG. 2.

The principles of the present invention may be understood with reference to the analysis of plasma for the cholesterol content. The cholesterol ester in the plasma is converted by cholesterol ester hydrolase (CE) by the following enzymatic reaction 1:

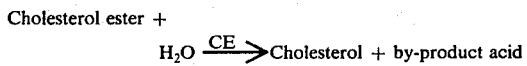
Cholesterol ester + H₂O $\xrightarrow{CE}$ Cholesterol + by-product acid Both the cholesterol released from the above ester reaction and the free cholesterol in the plasma reacts in the presence of oxygen (O$_2$) and cholesterol oxidase (CO) to produce cholestenone and hydrogen peroxide according to the reaction 2:

Cholesterol $\xrightarrow[O_2]{CO}$ Cholestenone + H$_2$O$_2$

In the polarographic apparatus of FIG. 1, the electrode probe 5 oxidizes a constant portion of the hydrogen peroxide at the platinum anode 6 as most probably illustrated by reaction 3:

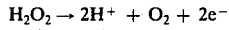
$$H_2O_2 \rightarrow 2H^+ + O_2 + 2e^-$$

The circuit is completed by a silver cathode 7 at which oxygen is reduced to water as most probably illustrated by reaction 4:

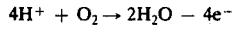
$$4H^+ + O_2 \rightarrow 2H_2O - 4e^-$$

Relating the above reactions to the principles of operation in FIG. 1 of the drawing, FIG. 1 is a diagrammatic illustration of an apparatus illustrating the polarographic cell 9 with electrode probe 5 and sample cuvet or chamber 8. In the detailed operations which follow, a modified Model 23 Yellow Springs Instrument Company glucose analyzer was employed and it is here described as follows. The cell is provided with its own potential source which in this case is a battery 10 using an applied voltage of about 0.6 volts. The positive pole of the battery 10 is attached to the platinum polarographic anode 6 having a face 11 diameter of 0.5 mm with an adjacent silver reference cathode 7 having an active surface area 12 of about 0.5 square cm. Full scale output is of the order of magnitude of 100 nanoamperes. A G-2500 Varian strip chart recorder, not shown, was used to make the current measurements. The electrode probe 5 is only diagrammatically shown including an insulating support member 13 and the electrodes are also insulated from one another. The tip of the electrode probe is covered by a cellophane membrane 14 (1⅛ in. dialysis tubing, A. H. Thomas Co., Cat. No. 4465-A2) which serves to protect the electrodes and to define a diffusion path to them from the sample chamber 8 having a volume of 0.40 ml and thermostated at 38° C. Membrane 14 is mounted to the electrode probe by an O ring 15. The cellophane membrane 14 is permeable enough to readily pass hydrogen peroxide, water, oxygen and salt, but impermeable to the material being measured, certain interferring substances such as catalase, and the enzyme which provides the reaction in the presence of oxygen to liberate hydrogen peroxide. Positioned at the side of the sample chamber 8 is a thin oxygen permeable membrane, such as silicone rubber, which permits the passage of air or oxygen from a stirring pump into the enzyme-electrolyte mixture contained in the sample chamber 8 and the gas is eliminated through the vent. The active face 11 of the anode is spaced a capillary distance from the cellophane membrane 14 and is in contact with the electrolyte mixture. As mentioned, the reference silver cathode surface 12 is positioned adjacent the platinum anode face 11 and also contacts the electrolyte mixture. A syringe for injection of plasma sample is shown along with buffer supply, injection port, septum cord and waste removal, thereby illustrating flow of sample analysis. A typical schematic electrical system includes a galvanometer 16 which will read the current created by the enzymatic-cholesterol reaction by detecting the hydrogen peroxide by-product of the reaction. The current thus created is directly proportional to the cholesterol level in the plasma sample. A further detailed description of polarographic electrode systems and structure of the type exemplified in FIG. 1 may be had by reference to my U.S. Pat. No. 3,539,455 and this description is incorporated herein by reference.

In operation, the membrane polarographic instrument of FIG. 1 is used for the quantitative determination of cholesterol which is convertible by an enzyme to produce ultimately hydrogen peroxide. Aqueous electrolyte and buffer solution is introduced into the sample chamber 8. Cholesterol oxidase and esterase enzymes are both introduced into the sample chamber 8 on the side of the membrane 14 opposite the electrode for enzymatic reaction with the cholesterol in a plasma sample to produce ultimately hydrogen peroxide. The plasma sample under analysis is introduced into the chamber 8 by means of the syringe through the septum cord. Oxygen is provided by the stirring pump through the permeable silicone rubber membrane into the vented sample chamber. Thus, the quantity of plasma containing the cholesterol to be analyzed and the enzymes are located on the side of the membrane opposite the electrode probe 5. As the cholesterol, both free and combined, in the plasma comes into contact with the enzyme system of CO and CE, the enzymatic reaction takes place in the presence of oxygen as described above to produce cholestenone and hydrogen peroxide. The hydrogen peroxide in turn diffuses into the cellophane membrane and into contact with the platinum anode. At this point, the reactions at the platinum anode and the silver cathode above described take place. Thus, a current is yielded and flows across the cell directly proportional to the quantity of hydrogen peroxide diffused. The determination of the current flowing across the cell by the galvanometer 16 is a function of the amount of hydrogen peroxide formed and is an indication of the amount of cholesterol in the plasma. The enzymatic reaction need not be complete because the polarographic anode measures the rate of formation of the hydrogen peroxide.

In the practice of the presently most preferred embodiment, the following materials and methods were employed in the determination of cholesterol.

Cuvet Reagent — The composition of the cuvet reagent is summarized in Table I. The pH was adjusted to 6.6 using the two phosphate salts.

TABLE I

| SUBSTANCE | CONCENTRATION gm/100 ml | FUNCTION |
| --- | --- | --- |
| $KH_2PO_4$ (0.5M) | 13.0 | Buffer |
| $K_2HPO_4$ (0.5M) | 8.7 | Buffer |
| Sodium azide | 0.07 | Inhibit catalase |
| Sodium taurocholate | 0.30 | Hydrolase co-factor |
| Triton X-100 | 0.05 | "Solubilize" cholesterol |
| Potassium chloride | 1.0 | Stabilize Ag cathode |

The functions served by the cuvet reagent constituents are also summarized in above Table I. Sodium azide, used as a buffer preservative and a catalase inhibitor, was also effective in stabilizing hydrogen peroxide injected in the cuvet. As developed above, because of the high levels of catalase in whole blood, it was not possible to perform the unbound enzyme assay in either whole blood, or blood which was severly hemolyzed.

Enzymes — Cholesterol oxidase (CO) [Enzyme Commission No. 1.1.3.6] was derived from Nocardia or from Brevi bacterium sp. The CO was reconstituted by dissolving 9.4 U of enzyme in 1 ml of 1% Triton X-100 (a nonionic alkaryl polyether by Rhom & Haas); enzyme activity is reported as International Units (U). Cholesterol ester hydrolase (CO) [Enzyme Commission No. 3.1.1.13] was prepared from beef pancreas and it was reconstituted by dissolving 9.4 U in 1 ml of 1% Triton X-100.

Cholesterol standards — Cholesterol was purified by crystallization from acetone and dried over silica gel. It was emulsified in surfactant solution using a Branson Model J17A sonicator. Suitable cholesterol emulsion standards are prepared containing 200 mg% in 1% solution stearate with the pH adjusted to 7.1, or 200 mg% in Triton X-100. Commercially prepared standards were also used for derivation of dilution curves. Pooled human plasma, preanalyzed repetitively by the AA-II colorimetric methodology ("Lipid Research Clinics Program", Manual of Laboratory Operations, National Heart and Lung Institute, Bethesda, Md., vol. 1 [1974]) was used to derive standard curves for analysis of human plasma samples.

Prior to assaying human plasma samples by cholesterol electrode method of this invention, and for comparison with AA-II colorimetric technology, experimental conditions including enzyme concentration, temperature, pH, reaction duration, etc., and machine sensitivity settings were analyzed singly and in combination, to determine optimal conditions as follows.

Cholesterol oxidase concentration — Initial studies of electrode response to CO injection were done using 50 $\mu$ 1 of dog plasma and various amounts of CO. The most stable and reproducible responses were observed with 0.15 U of CO, with a stable reading at 6-8 minutes. Using higher amounts of CO (1.93, 0.99 and 0.522 U), a peak activity could be obtained at 2, 3 and 4 minutes respectively, but total electrode response did not differ from that observed with 0.14 U. Using 50 $\mu$ 1 of human plasma, optimal electrode response was observed using 0.15 U, with higher amounts of enzyme producing variable results and lower amounts giving reactions which did not come to a peak stable level.

Cholesterol esterase concentration — Using 50 $\mu$ 1 of human plasma and 0.15 U of CO, serial studies were made of various concentrations of CE. Maximal electrode response was recorded in a range between 0.094 to 0.40 U, with the most reproducible response curves obtained at 0.2 U. It was also apparent that simultaneous injection of the CO and CE produced the same readings for total cholesterol (within 6-8 minutes) as a separate pre-incubation of CE with plasma, and then injection of the plasma-CE mixture along with CO.

Effect of temperature — Using 50 $\mu$ 1 of plasma, and the optimal concentrations of CO (0.15 U) and CE (0.20 U), the effects of temperature were assessed. With temperatures at or below 30° C, reaction rates were very slow (12-15 minutes to reach peak electrode response), and total electrode response was low. Although linear standard curves could be obtained at these lower temperatures, they were very shallow, so that a moderate change in electrode response produced major changes in measured cholesterol level when read off the standard curve. At 50° and 60° C, reaction rates were faster (peak activities being reached at 2 minutes) with increased total electrometer readings. At these temperatures, however, electrode response was erratic, probably due to rapid deterioration of the cellophane membranes and loosening of the "O" ring which held the membrane. At 38° C, the temperature in current use, reaction rates were intermediate (4-8 minutes), the standard curves were linear, and there was excellent membrane duration, with membranes in active use for weeks without requiring change.

pH Optimum — The enzymatic reaction was stable over a wide range of pH as summarized in Table II.

TABLE II

| Effect of pH on electrode current in the presence of dog plasma and cholesterol oxidase and added cholesterol oxidase plus cholesterol ester hydrolase. | | | |
| --- | --- | --- | --- |
| | Peak Meter Reading | | Ratio |
| pH | Oxidase | Hydrolase | Free/Total |
| 3.9 | 154 | 322 | 1 2.10 |
| 5.0 | 153 | 346 | 1 2.30 |
| 6.1 | 172 | 336 | 1 1.95 |
| 6.8 | 153 | 336 | 1 2.20 |
| 8.1 | 174 | 360 | 1 2.10 |
| 8.9 | 182 | 375 | 1 2.10 |
| 10.7 | 193 | 403 | 1 2.10 |

The pH of the cuvet reagent was adjusted with phosphoric acid or a concentrated potassium hydroxide solution. After filling the cuvet with the appropriate buffer, a 50 $\mu$l of dog plasma was injected, followed by CO. After reaching a peak current, CE was then injected and the current was recorded after it had peaked and stabilized. The pH of 6.6, used in the final assay method, was selected for convenience.

After having derived optimal cuvet reagents, enzyme concentrations, and reaction conditions, the following measurements of plasma cholesterol were made, with evaluation of various preassayed or weighed standard cholesterol solutions, derivation of dilution curves, and studies of precision, accuracy, sensitivity and specificity.

Plasma, Sample Preparation and Analysis — All plasma samples were collected by venipuncture in EDTA containing tubes, after a 12-14 hour fast, and the plasma separated by centrifugation at 4° C. Blood from small animals was collected by orbital bleeding or heart puncture. The cuvet for the analyzer was arranged so that it was repetitively rinsed between analyses with 0.5 M phosphate buffer at 38° C and a pH 6.6. Subsequent to rinsing, the cuvet was drained and filled with cuvet reagent having the composition shown in Table I. Plasma (20–50 µl) was then injected using a microliter syringe, followed by 25 µl of cholesterol oxidase (0.15 U), and 20 µl of CE (0.20 U). The electrode response was read after a stable current reading was obtained (from 4–8 minutes). For measurement of free and esterified cholesterol, the plasma was first injected, followed by an injection of CO. After a stable current response was obtained for free cholesterol, the CE was injected, with a second stable reading obtained for the cholesterol esters. After analysis of each plasma sample, the cuvet was rinsed with phosphate buffer three times, and the next sample was introduced.

Initially, cholesterol suspensions were measured with the apparatus of FIG. 1 as described above. As summarized in FIG. 3, the polarographic curve for crystalline cholesterol in 1% Triton X-100 was almost identical to that for plasma. Then, dilution curves using known crystalline cholesterol samples in 1% Triton X-100 (Curve A) and diluted pre-assayed standard plasma samples (Curve B) were obtained (FIG. 4). The FIG. 4 meter readings merely represent uncalibrated current flow at current peaks for each of the samples as plotted against each sample's preassayed cholesterol content. FIG. 4 dilution plots were highly linear ($r=0.999$, 0.993), from 12.5–300 mg/100ml. Accordingly, the current readings were directly proportional to the cholesterol content of the samples and establish the method validity. Because no artificial emulsion can satisfactorily mimic plasma, these serial studies of human plasma cholesterol were done using preassayed reference plasma standards, measured by the above referred to AA-II colorimetric method.

In determination of serial standard dilution curves, it was apparent that there was a gradual, and in most cases, minor reduction in sensitivity with time, which resulted in a parallel downward shift in the standard dilution curve, without change in slope or linearity. To assure most accurate and precise results, it was necessary to run two or more standard dilution curves daily with an occasional reference plasma included in the unknown samples to check on sensitivity.

The precision of the cholesterol electrode method was evaluated using multiple aliquots from pooled, preassayed reference plasmas with analyses of same-day and inter-day precision. The same-day coefficient of variation was calculated by measuring the cholesterol content of 20 aliquots from a single preassayed reference plasma pool, with a total cholesterol content of 230 mg/100ml. The coefficient of variation was 1.3% for this "same-day" analysis. The inter-day precision of the cholesterol electrode system was evaluated using multiple aliquots from the preassayed reference plasma pool of 230 mg/100ml. The coefficient of variation, measured in 2 aliquots from this pool over a 10 day period (20 total samples) was 1.2%.

The accuracy of the cholesterol electrode method was evaluated using paired comparisons with duplicate aliquots run by the above AA-II colorimetric method. 120 plasma samples obtained from screening studies were used, with a range of values for plasma cholesterol from 126–381 mg/100ml. Cholesterol levels determined by the two methods were highly correlated ($r=0.914$, $p$ <0.001), with mean ± SEM levels for the colorimetric and electrode methods being 175 ± 3.3 and 168 ± 2.6 mg/100ml, respectively. The mean difference of 7.06 mg/100ml, with the colorimetric method being regularly higher than the cholesterol electrode method, was significant by paired testing of differences ($p < 0.001$), but represented only a 4% difference between methodologies. When 25 µl of a crystalline cholesterol emulsion (100 mg/100ml) was added to 25 µl of plasma (115 mg/100ml), recovery was 97% of expected values.

Bound-enzyme method — The bound-enzyme method of this invention was performed using the probe 17 of FIG. 2 having a collagen membrane 18 and glutaraldehyde-bound cholesterol oxidase (CO) 19. After fitting the collagen membrane 17 over the electrode as described with reference to FIG. 1, the membrane was carefully covered with a very thin layer of 25% glutaraldehyde. About 20 U of crystalline CO was then gently placed on the surface of the glutaraldehyde-treated membrane, and a drop of glutaraldehyde was placed on top of the enzyme. The bound-enzyme electrode was then air-dried for 30 minutes and inserted into the cuvet chamber 8 in place of probe 5 of FIG. 1. When using the membrane bound-enzyme system, the plasma and CE were injected as noted above, without supplemental injection of CO. For analytical purposes, once a stable reading had been obtained after this injection, the standard injection of CO was made to determine what amount of enzyme-substrate reactivity there was in excess of that provided by the bound enzyme system. Using the bound-cholesterol oxidase membrane system of FIG. 2, with injection of plasma and cholesterol esterase, linear plasma standard curve (Curve C) was also obtained (FIG. 4). The electrometer response was about 1/10th that of response with the free injected oxidase.

The membrane bound enzyme also unexpectedly affords a means to analyze whole blood directly without need for catalase inhibition. In such anaylsis, the enzyme reaction rate (i.e., $H_2O_2$ formation) occurring in or immediately adjacent enzyme layer 19 can be detected at the anode to indicate the cholesterol content in the whole blood sample. Current readings have been obtained even though $H_2O_2$ would be expected to diffuse into the sample chamber for destruction by the catalase.

Employing the techniques above described for the determination of cholesterol in blood plasma, similar analyses were made of blood plasma of other animals as shown in the following Table III.

TABLE III

| Animal Plasma | Free Cholesterol | | Cholesterol Esters | |
|---|---|---|---|---|
| | Peak Reading | Minutes to Peak | Peak Reading | Minutes to Peak |
| Mouse | 112 | 0.5 | 320 | 2.0 |
| Rat | 55 | 0.5 | 288 | 2.0 |
| Gerbil | 99 | 0.8 | 314 | 3.0 |
| Rabbit | 90 | 0.8 | 289 | 1.3 |

Analyses of a variety of other liquids is given in Table IV.

TABLE IV

| | PEAK METER READINGS | |
|---|---|---|
| Sample | Free Cholesterol | Cholesterol Esters |
| Egg yolk 1/4 with $H_2O$ | 643 | 0 |
| Mouse brain homogenate 1/6 | 454 | 474 |
| Whipping cream | 340 | 0 |
| 3.5% butterfat milk | 102 | 141 |
| Non-dairy creamer | 50 | 94 |

TABLE IV-continued

| | PEAK METER READINGS | |
|---|---|---|
| Sample | Free Cholesterol | Cholesterol Esters |
| Human semen | 215 | 0 |
| Lobster tail homogenate 1/6 | 121 | 0 |
| Shrimp homogenate 1/8 | 111 | 0 |
| Juice from shrimp | 122 | 0 |
| Oyster homogenate 1/3 | 89 | 0 |

Tables III and IV provide current peak values for free cholesterol and cholesterol esters in animal bloods and a variety of liquids. The ratios of free versus ester cholesterol contents are more or less in agreement with data available in the literature.

As discussed above, the electrodes are in electrically insulating relation and the electrolyte material occupies the sample chamber to provide an electrical path between two electrodes. Typical electrolytes include sodium or potassium chloride buffers including carbonate, phosphate, bicarbonate, acetates or alkali or rare earth metals, or other organic buffers or mixtures thereof. The solvents for such electrolyte may be water, glycols, glycerin and mixtures thereof. The electrodes above described were a platinum anode and associate silver cathode, but these are representative of other electrodes which one of ordinary skill may employ in order to practice the method of this invention. In addition to the cellophane and collagen membranes employed above, other membranes which are impermeable to the macromolecules under investigation but permeable to hydrogen peroxide may be employed. The invention is not limited to a particular membrane. Furthermore, the oxygen permeable membrane which is a silicon plastic rubber may be substituted by other materials as described in my U.S. Pat. No. 3,539,455. While features of the present invention have been described in detail with reference to the analysis of bloods and other liquids to determine the cholesterol content thereof, it will be apparent to those skilled in the art that the invention, in view of this description, has broader application to other macromolecular materials for enzymatic reaction on the membrane side of the electrode and where the hydrogen peroxide by-product of the reaction permeates the membrane for detection by the polarographic anode. Thus, variations of the methods disclosed may be made without departing from the spirit and scope of this invention.

What is claimed is:

1. A method for quantitative polarographic determination of a substance which is convertible by at least one enzyme to produce ultimately hydrogen peroxide comprising the steps of
   providing a polarographic cell including at least one electrode sensitive to hydrogen peroxide positioned behind a membrane permeable to hydrogen peroxide and impermeable to said substance being measured, said cell containing an electrolyte,
   at least one enzyme contained in said cell on the side of the membrane opposite said electrode for enzymatic reaction with said substance to produce ultimately hydrogen peroxide,
   establishing a potential across said cell such that current is produced which is proportional to the amount of hydrogen peroxide produced,
   adding a quantity of material containing said substance for said enzymatic reaction on the side of the membrane opposite said electrode and to effect diffusion of at least a portion of said hydrogen peroxide into said membrane and into contact with said electrode, and
   determining the current flowing across said cell as a function of the amount of hydrogen peroxide formed and as an indication of the amount of said substance in said material.

2. The method of claim 1 wherein the substance being measured is a sterol.

3. The method of claim 2 wherein said sterol is cholesterol and said enzyme is cholesterol oxidase.

4. The method of claim 2 wherein said sterol is a 3-betahydroxy sterol and said enzyme is cholesterol oxidase.

5. The method of claim 1 wherein said material is selected from the group consisting of blood plasma and blood serum and the substance being measured is cholesterol.

6. The method of claim 5 wherein said material additionally contains cholesterol esters and cholesterol ester hydrolase enzyme is present to convert said cholesterol esters to cholesterol.

7. The method of claim 1 wherein the enzyme is immobilized on the side of the membrane opposite said electrode.

8. The method of claim 1 wherein the enzyme is immobilized on the membrane.

9. The method of claim 8 wherein said material is whole blood.

10. The method of claim 7 wherein the enzyme is selected from the group consisting of cholesterol oxidase, cholesterol ester hydrolase and mixtures thereof.

11. The method of claim 1 wherein said substance is a polysaccharide which is convertible by said enzymatic reaction to substrates which by further enzymatic reaction produce ultimately hydrogen peroxide.

12. The method of claim 11 wherein said polysaccharide is a starch which is convertible by enzymatic reaction to a compound selected from the group consisting of mono and disaccharides, and wherein at least a second enzyme is present for further enzymatic reaction with said mono or disaccharide to produce ultimately hydrogen peroxide.

13. The method of claim 1 wherein said electrode is a platinum anode.

14. The method of claim 13 including a silver cathode.

15. A method for the quantitative determination of cholesterol in blood which comprises the steps of
   providing a polarographic cell including at least one electrode sensitive to hydrogen peroxide positioned behind a membrane permeable to hydrogen peroxide and impermeable to cholesterol,
   separating from said blood the component selected from the group consisting of blood plasma and blood serum,
   introducing cholesterol oxidase into said cell on the side of the membrane opposite said electrode for enzymatic reaction with cholesterol to produce hydrogen peroxide,
   providing oxygen in said cell for said enzymatic reaction,
   establishing a potential across said cell such that current is produced which is proportional to the amount of hydrogen peroxide produced,
   adding a quantity of said component for reaction with said enzyme and to effect diffusion of at least a portion of said hydrogen peroxide into said membrane and into contact with said electrode, and determining the current flowing across said cell as a function of the amount of hydrogen peroxide formed and as an indication of the amount of cholesterol in said blood.

16. The method of claim 15 wherein said component is slightly hemolyzed and further contains an anti-catalase agent.

17. The method of claim 16 wherein said agent is sodium azide.

18. The method of claim 15 which also includes cholesterol ester hydrolase for enzymatic reaction with said component.

19. The method of claim 15 wherein the polarographic cell includes a platinum anode sensitive to hydrogen peroxide and an adjacent silver cathode.

20. The method of claim 15 wherein said membrane is a cellophane membrane.

21. The method of claim 15 wherein the enzyme is immobilized in the membrane side opposite said electrode.

22. A method for the quantitative determination of cholesterol in whole blood which comprises the steps of providing a polarographic cell including at least one electrode sensitive to hydrogen peroxide positioned behind a membrane permeable to hydrogen peroxide and impermeable to cholesterol, immobilizing cholesterol oxidase on the membrane on the side opposite said electrode for enzymatic reaction with cholesterol to produce hydrogen peroxide, providing oxygen in said cell for said enzymatic reaction, establishing a potential across said cell such that current is produced which is proportional to the amount of hydrogen peroxide produced, adding a quantity of said blood for reaction with said enzyme and to effect diffusion of at least a portion of said hydrogen peroxide into said membrane and into contact with said electrode, and determining the current flowing across said cell as a function of the amount of hydrogen peroxide formed and as an indication of the amount of cholesterol in said blood.

23. The method of claim 22 which also includes cholesterol ester hydrolase immobilized on said membrane on the side opposite said electrode for enzymatic reaction with said blood.

* * * * *